United States Patent
Hochstetter et al.

(10) Patent No.: US 8,627,713 B2
(45) Date of Patent: Jan. 14, 2014

(54) METHOD FOR PREDETERMINING THE FATIGUE LIFE OF POLYMER COMPOSITION

(75) Inventors: Gilles Hochstetter, Bernay (FR); Lionel Hugon, Menneval (FR); Frédéric Demanze, Caudebec en Caux (FR); Stéphanie Pignoc-Chicheportiche, Le Trait (FR)

(73) Assignees: Arkema France, Colombes (FR); Technip France, Courbevoie (FR)

( * ) Notice: Subject to any disclaimer, the term of this patent is extended or adjusted under 35 U.S.C. 154(b) by 303 days.

(21) Appl. No.: 13/062,615

(22) PCT Filed: Sep. 8, 2009

(86) PCT No.: PCT/FR2009/051691
§ 371 (c)(1),
(2), (4) Date: May 23, 2011

(87) PCT Pub. No.: WO2010/026356
PCT Pub. Date: Mar. 11, 2010

(65) Prior Publication Data
US 2011/0214509 A1 Sep. 8, 2011

(30) Foreign Application Priority Data

Sep. 8, 2008 (FR) .................................. 08 56029

(51) Int. Cl.
*G01M 1/00* (2006.01)
*G01N 3/08* (2006.01)
(52) U.S. Cl.
USPC ........................................................ 73/65.07
(58) Field of Classification Search
USPC ........................................ 73/834, 826, 65.01
See application file for complete search history.

(56) References Cited

U.S. PATENT DOCUMENTS 5,165,287 A * 11/1992 Manahan, Sr. .................. 73/851
5,305,645 A * 4/1994 Reifsnider et al. .............. 73/808
(Continued)

FOREIGN PATENT DOCUMENTS

EP 0 487 691 B1 7/1995
EP 1 044 806 10/2000
(Continued)

OTHER PUBLICATIONS

International Search Report of PCT/FR2009/051691, Date of Completion Nov. 23, 2009, Date of Mailing Dec. 14, 2009.
(Continued)

*Primary Examiner* — Lisa Caputo
*Assistant Examiner* — Jamel Williams
(74) *Attorney, Agent, or Firm* — Millen, White, Zelano & Branigan, P.C.

(57) ABSTRACT

The invention relates to a method for evaluating the fatigue life of a polymer composition, including the following steps: i) providing a polymer composition; ii) manufacturing a plurality of axisymmetric test tubes cut from said composition; iii) subjecting said test tubes to a uniaxial traction fatigue test including a plurality of loading and unloading cycles for the test tube, the geometry of the test tube making it possible to subject the material to triaxial stresses, in the area of the test tube cut, simulating the stress conditions for the pressure sheath of a flexible pipe, particularly for off-shore use; and iv) predetermining the number of cycles until the rupture of said polymer composition. The invention is related to the use of said polymer composition selected through the predetermining method for manufacturing pipes or conduits to convey a pressurized and/or corrosive fluid.

13 Claims, 3 Drawing Sheets

(56) References Cited

U.S. PATENT DOCUMENTS

| | | |
|---|---|---|
| 6,271,294 B1 | 8/2001 | L Asson et al. |
| 6,376,586 B1 * | 4/2002 | Pascal et al. ............ 524/225 |
| 6,491,994 B1 | 12/2002 | Kito et al. |
| 6,881,460 B2 | 4/2005 | Inaba et al. |
| 7,132,073 B2 | 11/2006 | Inaba et al. |
| 2002/0155242 A1 | 10/2002 | Bellet et al. |
| 2003/0099799 A1 | 5/2003 | Koike et al. |
| 2003/0157335 A1 | 8/2003 | Inaba et al. |
| 2003/0220449 A1 * | 11/2003 | Jacques et al. ............ 525/178 |
| 2004/0060642 A1 | 4/2004 | Inaba et al. |

FOREIGN PATENT DOCUMENTS

| | | |
|---|---|---|
| EP | 1 260 747 | 11/2002 |
| EP | 1 270 208 | 1/2003 |
| EP | 1 283 101 | 2/2003 |
| EP | 0884 358 B | 7/2003 |
| EP | 0 608 939 B | 4/2006 |
| EP | 1 342 754 B | 3/2008 |
| JP | 07 103871 | 4/1995 |
| JP | 09 229833 | 9/1997 |
| WO | WO 93/22651 A | 11/1993 |
| WO | WO 2006/097678 A1 | 9/2006 |

OTHER PUBLICATIONS

Tao G et al: "A non-contact real-time strain measurement and control system for multiaxial cyclic/fatigue tests of polymer materials by digital image correlation method", Polymer Testing, Elsevier, vol. 24, No. 7, Oct. 1, 2005, pp. 844-855, XP 025280072, ISSN: 0142-9418.
Office Action for related Japanese Application No. 2011-525604; dated May 28, 2013.
English Translation of Office Action for related Japanese Application No. 2011-525604 dated May 28, 2013.
International Search Report of PCT/GB2006/000723, Date of Completion May 12, 2006, date of Mailing May 30, 2006.
Mitsubishi Heavy Ind. Ltd.; Sample Piece Used Under Biaxial Tensile Stress and Test Method Using the Same; English Abstract of JP09-229833, dated Sep. 5, 1997.
Nippon Steel Corp; Method for Evaluating Fatigue Fracture Sensibility at Part Subjected to Welding Heat; English Abstract of JP07-103871, dated Apr. 21, 1995.

* cited by examiner

METHOD FOR PREDETERMINING THE FATIGUE LIFE OF POLYMER COMPOSITION

FIELD OF THE INVENTION

The present invention relates to a process for evaluating the fatigue life of a polymer composition. A polymer composition selected by means of the evaluation process makes it possible to produce pipes or other articles capable of withstanding extremely severe usage conditions, such as those encountered in the offshore oil industry. The invention also relates to a pipe for transporting a petroleum fluid, which has this polymer composition selected by means of the process for evaluating the fatigue life.

TECHNICAL PROBLEM

The exploitation of oil reserves located offshore subjects the equipment and material used, and in particular the conduits or pipes used to transport the hydrocarbons thus extracted, to extreme conditions. Indeed, the hydrocarbons are generally transported at high temperature (up to 135° C.) and high pressure (greater than 1000 bar). During the operation of the installations, severe problems of mechanical strength (pressure resistance, abrasion resistance), thermal resistance and chemical resistance of the materials used are therefore faced. Such conduits and pipes must in particular be resistant to hot oil, to gas, to the surrounding salt water and to the mixtures of at least two of these products for periods which may stretch to 25 years.

Conventionally, these pipes comprise a metallic inner layer that is not impermeable to oil and to water, formed by a profiled metal tape wound in a helix, such as an interlocked strip. This metallic inner layer, which gives shape to the pipe, is coated, in general by extrusion, with a polymer layer intended to confer impermeability. Other protective and/or reinforcing layers such as plies of metal fibers and rubbers may also be placed around the impermeable polymer layer.

For operating temperatures below 60° C., the polymer is HDPE (high-density polyethylene). For temperatures between 60° C. and 90° C., polyamide is used; up to 90° C. it is also possible to use crosslinked polyethylene (PEX) when the pressure is not too high. For temperatures above 90° C., in particular between 100° C. and 130° C., fluoropolymers are generally used such as PVDF (polyvinylidene fluoride) or a copolymer of vinylidene fluoride (VDF).

Polyamides and especially the polyamide PA-11 and fluoropolymers and especially the poly(vinylidene fluoride) (PVDF) are known for their good thermal behavior, their chemical resistance, especially to solvents, their resistance to adverse weather and to radiation (UV, etc.), their impermeability to gases and to liquids and their electrically insulating quality. They are especially used for manufacturing pipes or conduits intended for transporting hydrocarbons extracted from oil reserves located offshore or onshore.

Other requirements are added to those indicated above, before or after the oil exploitation. Thus, when the pipes or conduits are being laid or lifted (unwound or wound) they may be subjected to impacts, which they must withstand at temperatures that vary depending on the depth at which these pipes or conduits are laid, and that may reach quite low values (for example −35° C.) and substantial deformations. A deformability of around 7% is favorable to (un)wind the pipes without damaging them. Finally, it is important for the properties of the pipes or conduits to remain almost constant over time, so as to ensure that they have a long service life and that there is a possibility of reusing them.

In order to try and meet all these requirements, both in the short term and in the long term, various types of pipes have already been proposed, these generally comprising one or more metallic components that guarantee mechanical rigidity, but that are not impermeable to the fluids transported, for example a spiral steel band, and also various layers based on polymer compositions that provide, in particular, the impermeability to the fluids extracted and to seawater and the heat shielding. These polymer compositions may, for example, be based on polyethylene, but this choice limits the usage temperature of the pipes to at most 60° C. They may also be based on fluoropolymers such as PVDF (polyvinylidene fluoride) which is suitable for higher maximum usage temperatures, which may for example reach 130° C., and give them excellent chemical resistance. However, PVDF is very rigid and for this reason homopolymers of VDF are often formulated or used as a blend with copolymers of VDF.

Finally, additional requirements appear during the manufacture of the pipes or conduits. Thus, it is obviously desirable that the processability of the polymer compositions be as easy as possible, which requires a viscosity suitable for the conversion process (typically extrusion).

For this purpose, it is preferable that the composition used does not have too low a viscosity (for example a melt flow index according to the standard ASTM D-1238 (at 230° C. with 5 kg) of less than 15 g/10 min).

The selection of a polymer composition is therefore crucial in order to withstand, without damage, the manufacturing conditions, handling conditions, conditions for laying offshore flexible pipes and also good usage conditions. The construction of flexible hoses is complex. The juxtaposition of polymer layers and of metallic components (carcass, spiral reinforcements, etc.) results in subjecting the polymer used to locally triaxial deformations and stresses, in particular when the flexible hoses are bent. This occurs repeatedly, during the various operations for handling and laying flexible hoses. This is also the case during the use, in particular for dynamic applications such as for the flexible hoses that connect the seabed to the surface ("risers") and which are subjected to the swell.

The Applicant has developed a process for evaluating the fatigue life of polymer compositions that makes it possible to select those which meet the criteria listed above and which have advantageous technical features, especially fatigue resistance under triaxial stresses which is expressed by a high number of cycles to failure (NCF), for example of greater than 500.

The new criterion based on the fatigue resistance makes it possible to better design polymer compositions and materials that are compatible for use as a pressure sheath and intermediate sheath or external sheath of offshore flexible pipes. This is particularly true in the case of pressure sheaths made of a homopolymer or copolymer of VDF or blends thereof. The evaluation process according to the invention uses notched axisymmetric test specimens which are subjected to loading and unloading cycles, which constitute locally triaxial stresses that simulate the stresses of the pressure sheaths of an offshore flexible hose in service.

PRIOR ART

Application WO 2006/045753 describes a fluorinated polymer composition comprising a homopolymer of VDF, a fluorinated thermoplastic copolymer and a plasticizer, said composition having a ductile-brittle transition temperature of less than 5° C. The characterization parameters for anticipating the mechanical properties are the molecular weight expressed as relative viscosity measured in solution and in the melt state, and the ductile-brittle transition temperature of the polymer compositions measured as Charpy impact on notched test specimens. Mechanical properties such as the modulus E and the elongation at the yield point and the elongation at break are also measured.

Application WO 2006/097678 describes multilayer flexible pipes that contain a layer made of polyamide (PA-12). The only characterizing parameter mentioned in this application for anticipating the mechanical properties is the molecular weight expressed as relative viscosity, measured in solution.

Application EP 1 342 754 describes a composition for pipes that can be used in the exploitation of offshore oil and gas fields comprising a polyamide, a plasticizer and an NBR or H-NBR elastomer. Only the molecular weights are determined by size exclusion chromatography.

Document EP 0 608 939 describes polymer compositions intended for the manufacture of pipes for transporting hydrocarbons. The polymer compositions are based on a PVDF homopolymer, a thermoplastic copolymer of VDF and a plasticizer. Mechanical properties such as the elongation at the yield point and the elongation at break, and the IZOD impact strength are measured.

Studying the mechanical properties of various materials (metallic or polymer materials) with the aid of fatigue tests that use test specimens subjected to various stresses is known. The publication by Tao G. and Xia Z. (*Polymer Testing* 24, 2005, 844-855) describes a method which makes it possible to carry out uniaxial and biaxial fatigue tests on polymer materials of epoxy type. The test specimens used are either uniaxial or tubular. The biaxial stresses are obtained by superposing a tensile load and a torsional load on the test specimen. These methods are non-destructive and make it possible to develop a control system based on the digital image correlation technique.

None of these documents describes or suggests the determination of the fatigue life of polymer compositions which are intended, in particular, for the manufacture of pipes for transporting hydrocarbons or oil, satisfying a particular fatigue test that makes it possible to predict the mechanical strengths of these compositions in these pipes during the manufacture, installation and usage.

BRIEF DESCRIPTION OF THE INVENTION

More precisely, one subject of the invention is a process for evaluating the fatigue life of a polymer composition comprising the following steps:
(i) providing a polymer composition;
(ii) manufacturing several notched axisymmetric test specimens from said composition;
(iii) subjecting said test specimens to a tensile fatigue test comprising several uniaxial loading and unloading cycles of the test specimen inducing triaxial stresses therein that simulate the stress conditions of the pressure sheath of a flexible pipe, especially in an off-shore application; and
(iv) determining the number of cycles to failure for said polymer composition.

Surprisingly, it has been found that by working in fatigue, on notched axisymmetric test specimens, it is possible to subject the material tested to multiaxial fatigue stresses solely by using a tensile-testing machine, which makes it much simpler to carry out the tests in the laboratory. This is made possible by the notched axisymmetric geometry of the test specimen: thus, although the loading of the test specimen is unidirectional, the geometry of the test specimen makes it possible to induce triaxial stresses in the material, in the zone of the notch of the test specimen, which makes it possible to simulate the stress conditions of the pressure sheath of a flexible pipe, especially in an offshore application.

Each test specimen used in the process according to the invention is axisymmetric to the longitudinal axis z, having a maximum diameter d and a curved notch having a radius of curvature R. Each test specimen has in its notched part a minimum radius a, the a/R ratio ranging from 0.05 to 10 and d being greater than 2a and preferably ranging from 2a+0.5 R to 2a+2 R.

The tensile fatigue test consists of an elongation of the test specimen along the longitudinal axis, with a sinusoidal signal having a frequency ranging from 0.05 Hz to 5 Hz, preferably from 0.5 Hz to 2 Hz, at a temperature ranging from −15° C. to 23° C., preferably from −15° C. to 5° C., advantageously from −15° C. to −5° C., the maximum elongation of one and the same tensile fatigue cycle being chosen from 0.05 R to 1 R, preferably from 0.075 R to 0.4 R.

The compositions which have a mean number of cycles to failure (NCF) over several test specimens of >500, preferably of >1000, advantageously of >5000, more preferably still of >10 000 are selected.

According to a first embodiment of the invention, the minimum elongation of one and the same tensile cycle is greater than or equal to 0 up to 0.25 R and preferably up to 0.08 R.

According to another embodiment, since the radius of curvature R of the notch ranges from 0.5 mm to 10 mm, preferably from 3 mm to 5 mm, each test specimen has, in its notched part, a minimum radius a ranging from 0.5 mm to 5 mm, preferably from 1.5 mm to 2.5 mm; and a maximum diameter d ranging from 2 mm to 30 mm, preferably from 6 mm to 10 mm.

According to yet another embodiment, the maximum elongation along the longitudinal axis z ranges from 0.2 mm to 4 mm, preferably from 0.3 mm to 1.6 mm.

According to yet another embodiment, the ratio between the minimum elongation and the maximum elongation of the cycle is chosen from 0 up to 0.8 and preferably up to 0.5 and advantageously up to 0.25.

The polymer composition evaluated by means of the process according to the invention comprises at least one semicrystalline thermoplastic polymer having a glass transition temperature ($T_g$) of less than or equal to 130° C.

According to one embodiment, the polymer composition resulting from the determination process comprises a fluorinated polymer.

According to another embodiment, the polymer composition resulting from the determination process comprises a homopolymer or copolymer of VDF.

The invention also relates to a flexible metal conduit comprising one or more metallic components and also at least one layer comprising the polymer composition selected by means of the process according to the invention and optionally one or more layers of a polymer material different from that of the polymer composition.

Another subject of the invention relates to the use of notched axisymmetric test specimens for simulating the triaxial stresses of a polymer material, in particular that goes into the composition of a pressure sheath for a flexible pipe intended for an offshore use, in which each test specimen is subjected to a tensile fatigue test comprising several loading and unloading cycles of the test specimen.

DETAILED DESCRIPTION OF THE INVENTION

The polymer composition according to the invention comprises at least one semicrystalline thermoplastic polymer having a glass transition temperature (TO of less than or equal to 130° C., preferably of less than or equal to 110° C. The glass transition temperature may be measured by differential scanning calorimetry (DSC).

The polymer composition of the invention may furthermore also contain additives. As additives, plasticizers, impact modifiers and mixtures thereof may be chosen.

The semicrystalline thermoplastic polymer having a glass transition temperature (TO of less than or equal to 130° C. may especially be chosen, without limitation from:
- polyolefins such as polyethylene and polypropylene;
- thermoplastic polyurethanes (TPUs);
- polyethyleneterephthalate or polybutylene-terephthalate;
- silicone polymers;
- fluoropolymers comprising at least 50 mol %, and preferably constituted, of monomers of formula (I):

$$CFX=CHX' \qquad (I)$$

where X and X' independently denote a hydrogen atom or halogen atom (in particular fluorine or chlorine) or a perhalogenated (in particular perfluorinated) alkyl radical, and preferably X=F and X'=H, such as polyvinylidene fluoride (PVDF), preferably in α form, copolymers of vinylidene fluoride with, for example, hexafluoropropylene (HFP), fluoroethylene/propylene (FEP) copolymers, copolymers of ethylene with either fluoroethylene/propylene (FEP), or tetrafluoroethylene (TFE), or perfluoromethyl vinyl ether (PMVE), or chlorotrifluoroethylene (CTFE), some of these polymers being in particular sold by ARKEMA under the name Kynar®; and
- mixtures thereof.

Regarding the PVDF according to the invention, this is a homopolymer of vinylidene fluoride (VDF of formula $CH_2=CF_2$) or a PVDF copolymer, that is to say a copolymer of VDF comprising by weight at least 50% by weight of VDF and at least one other monomer copolymerizable with the VDF. The VDF content should be greater than 80% by weight, or better still 90% by weight, to ensure a sufficient mechanical strength at high temperature (that is to say a good creep resistance at 130° C.)

The comonomer may be a fluoromonomer chosen, for example, from vinyl fluoride; trifluoroethylene (VF3); chlorotrifluoroethylene (CTFE); 1,2-difluoroethylene; tetrafluoroethylene (TFE); hexafluoropropylene (HFP); perfluoro (alkyl vinyl)ethers such as perfluoro(methyl vinyl)ether (PMVE), perfluoro(ethyl vinyl)ether (PEVE) and perfluoro (propyl vinyl)ether (PPVE); perfluoro(1,3-dioxole); perfluoro(2,2-dimethyl-1,3-dioxole) (PDD). Preferably, the optional comonomer is chosen from chlorotrifluoroethylene (CTFE), hexafluoropropylene (HFP), trifluoroethylene (VF3) and tetrafluoroethylene (TFE). The comonomer may also be an olefin such as ethylene or propylene. The preferred comonomer is HFP.

Regarding the plasticizer according to the invention, this is described in a general manner in "Encyclopaedia of Polymer Science and Engineering", Wiley and Sons (1989), pages 568-569 and pages 588-593. The plasticizer must be compatible with the vinylidene fluoride homopolymer or copolymer. Preferably, in order to guarantee good low-temperature properties, this is a "low temperature" plasticizer, that is to say a plasticizer which does not solidify at −30° C. It is possible to choose the plasticizer from the plasticizers described in U.S. Pat. No. 3,541,039 or in U.S. Pat. No. 4,584,215 and mixtures thereof.

By way of example, the plasticizer that can be used in the invention may be dibutyl sebacate (DBS of formula $C_4H_9$—COO—$(CH_2)_8$—COO—$C_4H_9$), dioctyl phthalate (DOP) or NBSA (N-n-butyl-butylsulfonamide). High-performance plasticizers that can also be used in the invention are polymeric polyesters such as those derived from adipic, azelaic or sebacic acids and diols, and mixtures thereof, on condition, however that their number-average molecular weight is at least around 1500, preferably at least 1800, and does not exceed around 5000, preferably is less than 2500 g/mol. Polyesters with too high a molecular weight specifically result in polymer compositions having a lower impact strength. A polyester of adipic acid having a mean molecular weight of 2050 g/mol sold by CIBA under the trademark RHEOPLEX 904 could also be used. One high-performance plasticizer for the present invention is DBS which is easily incorporated with the PVDF.

Regarding the impact modifier, it is possible, according to the invention, to choose an impact modifier of core-shell type; this comprises at least one inner layer made of a soft polymer and a shell based on an acrylic polymer (that is to say the outer layer, also referred to as acrylic shell). Acrylic polymer means polymers which contain methacrylic and/or acrylic monomers. The impact modifier is in the form of particles, the mean diameter of which is generally at most 1 μm, preferably between 50 and 400 nm.

Manufacture of the Polymer Composition

The polymer composition used according to the present invention may be manufactured directly by synthesis: a polymerization. In this case, the polymer composition according to the invention comprises a semicrystalline thermoplastic polymer having a glass transition temperature ($T_g$) of less than or equal to 130° C.

The composition used according to the present invention may also be manufactured by melt blending the various constituents in any mixing device, and preferably an extruder.

The polymer composition is usually recovered in the form of granules.

The Polymer Composition

The polymer composition used according to the invention may be a VDF homopolymer that contains a plasticizer. The weight content of plasticizer with respect to the VDF homopolymer is within the range extending from 10 to 15%, preferably between 10 and 12%.

Another polymer composition according to the invention may be a VDF homopolymer that contains a plasticizer and an impact modifier. The weight content of plasticizer with respect to the total weight of the polymer composition is chosen from 1% to 5%, preferably from 2% to 4%. The weight content of impact modifier with respect to the total weight of the polymer composition is chosen from greater than or equal to 2% up to 10%, preferably from 6% to 9%.

The polymer composition according to the invention may also contain a homopolymer or copolymer of VDF.

Figure 1:
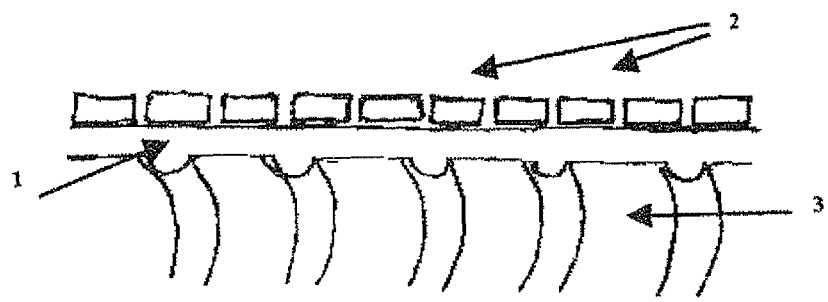
FIG. 1 represents a cross-sectional view of a flexible metal conduit comprising a layer of the polymer composition (1) covering a metal carcass (3), the whole assembly reinforced by armor (2).
Figure 2:
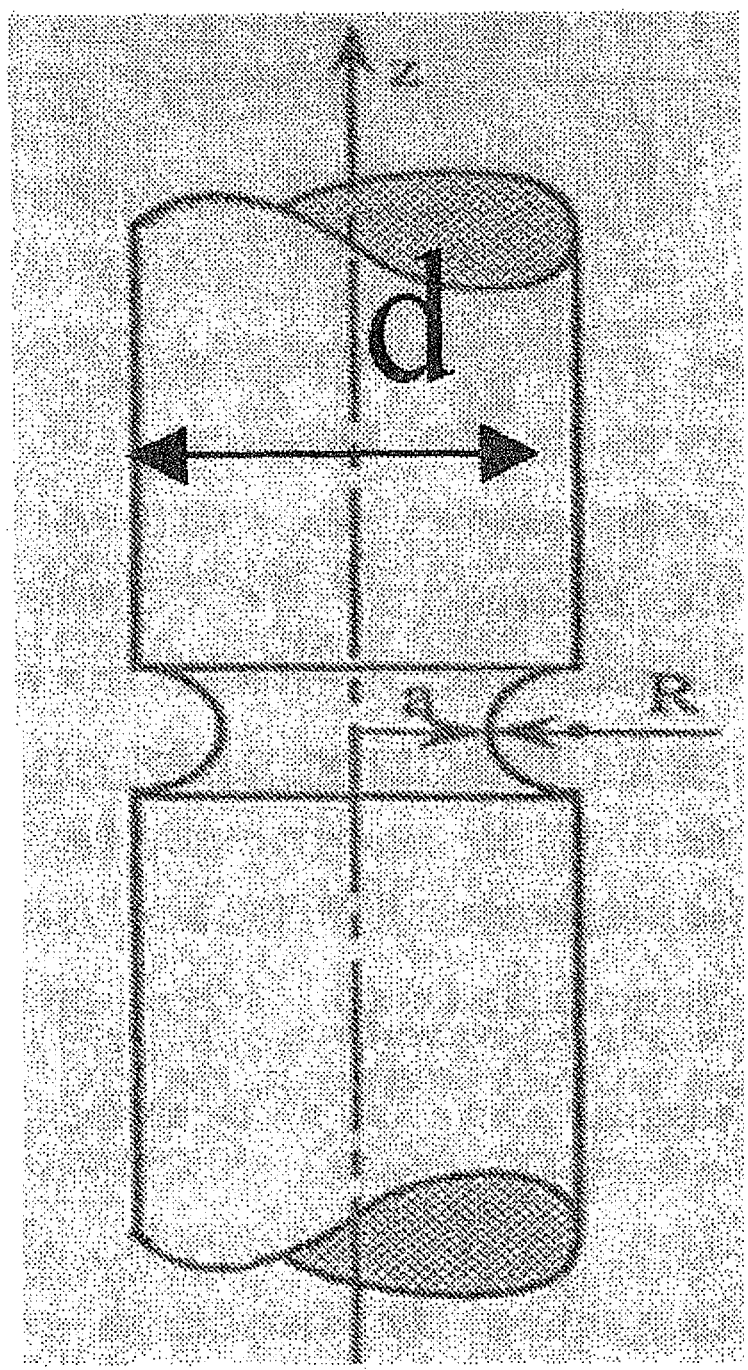
FIG. 2 represents the shape of an axisymmetric test specimen for the tensile fatigue test that makes it possible to impose a triaxial stress field on the stressed material: longitudinal axis z, comprising a curved notch or having a radius of curvature R, each test specimen having a minimum diameter a and a maximum diameter d.
Figure 3:
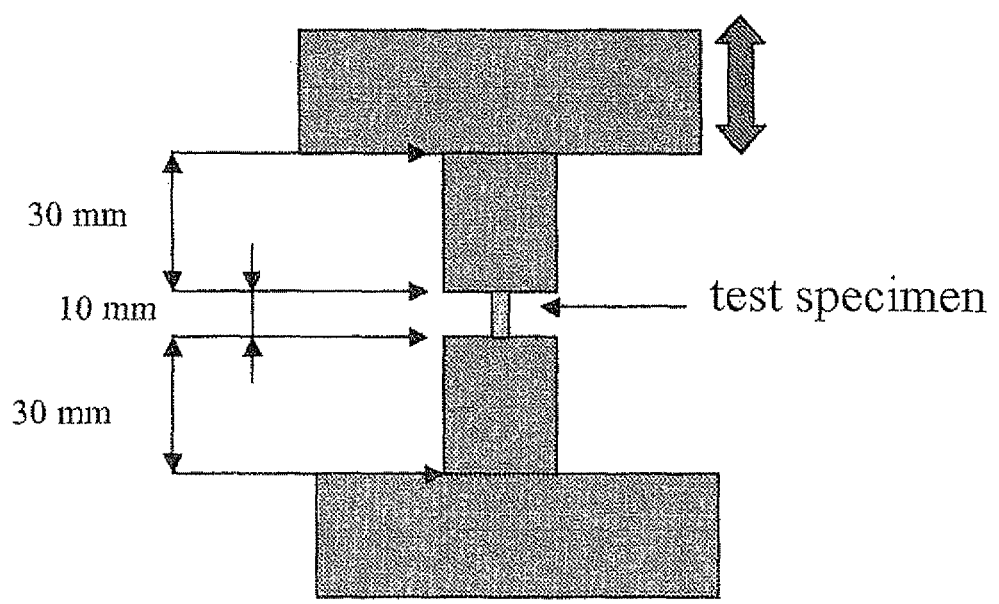

Definition of the abbreviations for the dimensions of the axisymmetric test specimen:
z—longitudinal axis a—minimum radius
R—radius of curvature
d—maximum diameter FIG. 3 schematically represents a servo-hydraulic testing machine with a test specimen.

TEST SPECIMENS

Test specimens for determining the fatigue life according to the invention are prepared from the polymer composition manufactured. The test specimens may be prepared by injection molding the polymer composition manufactured. Test specimens may also be prepared by extrusion, for example extrusion of strips or of tubes followed by a machining of the test specimens. In particular, the test specimens are cut out of the circular thickness of a tube of the polymer composition.

Each test specimen is axisymmetric to the longitudinal axis z and has a curved notch with a radius of curvature R, a minimum radius a and a maximum diameter d.

The test specimen is defined by these three values a, d and R.

The relationship between the minimum radius a and the radius of curvature, a/R, is from 0.05 to 10, preferably 0.2-1 and more preferably still 0.4-0.6.

The maximum diameter d is greater than 2 times the minimum radius a and preferably ranges from 2a+0.5 R to 2a+2 R.

In the production of a test specimen, the radius of curvature R is from 0.5 mm to 10 mm, preferably from 3 mm to 5 mm and typically 4 mm; each test specimen has a minimum radius a that varies from 0.5 mm to 5 mm, preferably from 1.5 mm to 2.5 mm and typically 2 mm; and the maximum diameter d is chosen from 2 mm to 30 mm, preferably from 6 mm to 10 mm and typically 7 mm.

It is known that the state of stress in a notched test specimen, subjected to a uniaxial tensile stress, is triaxial in the zone of the notch (Bridgman P. W. *Trans. Am. Soc. Met.* 1944, 32, 553). The smaller the radius of the notch, the greater the triaxiality. The test specimen with this shape makes it possible to impose on the material, under the conditions of the process according to the invention, a level of triaxiality of the stresses, representative of the stress conditions encountered by the polymer composition in a pressure sheath or an intermediate sheath or an external sheath of offshore flexible hose.

Fatigue Test

The fatigue test according to the invention consists in subjecting the test specimens to a tensile fatigue test that consists of an elongation along the longitudinal axis z, with a sinusoidal signal having a frequency ranging from 0.05 Hz to 5 Hz, preferably from 0.5 Hz to 2 Hz and typically 1 Hz, at a temperature ranging from −15° C. to 23° C., preferably from −15° C. to 5° C., advantageously from −15° C. to −5° C. and typically at −10° C.

The maximum elongation of a same tensile cycle is from 0.05 R to 1 R and preferably from 0.075 R to 0.4 R, expressed as a relative dimension starting from the radius of curvature of the notch R. The minimum elongation of a same tensile cycle is greater than or equal to 0 up to 0.25 R and preferably up to 0.08 R.

The maximum elongation is chosen from 0.2 mm to 4 mm, preferably from 0.3 mm to 1.6 mm and typically 1.4 mm.

The minimum elongation of the fatigue test is set by the ratio between the minimum elongation and the maximum elongation of the cycle. This ratio varies from greater than or equal to 0 up to 0.8 and preferably up to 0.5, and advantageously up to 0.25 and is typically 0.21.

The result of the fatigue test is the mean number of cycles to failure (NCF) of all of the test specimens. Various polymer compositions can be classified and compared from the results of this fatigue test: the larger the number of cycles to failure, the better the polymer composition.

The composition that has a mean number of cycles to failure (NCF) over several test specimens of >500, preferably >1000, advantageously >5000, and more preferably still >10 000 is selected.

Several is understood to mean that the number of measurements or of test specimens in order to calculate the mean number of cycles to failure (NCF) is at least 2, preferably between 2 and 50, advantageously between 5 and 40, and typically 10.

Use of the Polymer Compositions

The polymer composition selected by means of the determination process according to the invention may be used for manufacturing pipes or conduits intended for transporting a pressurized and/or corrosive fluid.

A flexible metal conduit may comprise one or more metallic components and also at least one layer comprising the polymer composition resulting from the manufacturing process according to the invention and optionally one or more layers of a polymer material different from that of the polymer composition.

EXAMPLES

The present invention will now be illustrated by examples of various polymer compositions, the use of which is the subject of the present invention.

Products Used
KYNAR® 400HDCM800: bimodal PVDF homopolymer sold by ARKEMA. This product contains DURASTRENGTH® D200: core-shell type impact modifier sold by ARKEMA having a soft inner layer with a $T_g \approx -40°$ C. and DBS: dibutyl sebacate (plasticizer). Other (non-commercial) versions contain EXL® 2650, instead of DURASTRENGTH, which is an impact modifier sold by Rohm & Haas having a soft inner layer with a $T_g \approx -60°$ C.
KYNAR® 50HDP900: bimodal PVDF homopolymer sold by ARKEMA that contains DBS.
KYNAR FLEX® 3120-50: copolymer of 90% by weight VDF and 10% by weight HFP (sold by ARKEMA) with a melting point between 161° C. and 168° C.

The ratios of the polymer compositions are by weight:
Composition A: 89% KYNAR 50 and 11% DBS
Composition B: 89.5% KYNAR 400 and 7.5% EXL 2650 and 3% DBS
Composition C: 100% KYNAR FLEX 3120-50
Composition D: 92% KYNAR 400 and 5% EXL 2650 and 3% DBS
Composition E: 95% KYNAR 400 and 2% D200 and 3% DBS Description of the Methods for Characterizing the Materials
Measurement of the Ductile-Brittle Transition (DBT) Temperature For the measurement of the ductile-brittle temperature (DBT), Charpy impact measurements were carried out by following a protocol derived from the test from the ISO 179 1eA standard. This protocol was adapted to be more severe than that of the standard in the sense that the notch was created using a razor blade and therefore had a notch tip radius smaller than the value of 0.25 mm recommended in the standard. The thickness of the bars used was also larger than that of the bars recommended in the standard (6 or 7 mm typically, versus 4 mm). The test was carried out, on 10 bars, by division into 5° C. steps in order to encompass the DBT. This corresponds to 50% brittle failure. The impact speed used as a reference was that recommended by the ISO 179 1eA standard.

Fatigue Test

This test consists in determining, for a given sample of polymer composition, the number of cycles to failure (NCF), that is to say the number of cycles at the end of which failure of the sample occurs. The larger the NCF is, the better the result of the fatigue test is for the given sample.

The test was carried out at a temperature of −10° C. on axisymmetric test specimens having a radius of curvature of the notch of 4 mm (R4) and a minimum radius of 2 mm, using a servo-hydraulic testing machine, for example of the MTS 810 type. The distance between the jaws was 10 mm. Imposed on the test specimen were: a maximum elongation of 1.4 mm and a ratio between the minimum elongation and the maximum elongation of 0.21, which resulted in a minimum elongation of 0.3 mm; with a sinusoidal signal having a frequency of 1 Hz. The result of the test is the mean of the results obtained over 10 test specimens. The logarithmic mean found for 10 test specimens corresponds to the NCF (mean number of cycles to failure).

Example: The polymer composition C has an NCF of 10 000 over the 10 test specimens tested. This means that there are, on average, 10 000 cycles before failure of the test specimens of the polymer composition.

Hot Creep

The hot creep resistance was evaluated by carrying out a tensile test at temperature in accordance with the ISO 527 standard on new test specimens of the polymer composition, with a conditioning of these test specimens at temperature for 20 min before the test. The yield strength of these test specimens is measured at 130° C. for polymer compositions based on homopolymers or copolymers of VDF. This strength corresponds to the nominal maximum tensile stress withstood by the test specimens before tension. The higher this strength is, the better the creep resistance of the polymer will be.

TABLE I

| Polymer composition | NCF in fatigue (R4, 1 Hz, −10° C., maximum elongation 1.4 mm, minimum elongation 0.3 mm) | DBT in Charpy impact (° C.) bars: 10 × 7 × 80, thin notch a/W = 0.2 | Hot creep [MPa] (at temperature) |
|---|---|---|---|
| A | 50 000 | −20 | 10 (130° C.) |
| B | 20 000 | −35 | 9.5 (130° C.) |
| C | 10 000 | −2 | 5 (130° C.) |
| D | 300 | −25 | 11 (130° C.) |
| E | 100 | −7.5 | 12 (130° C.) |

The results presented in table I above show that the classification of the polymer compositions A to E according to the Charpy test differs from that carried out on the basis of the fatigue test according to the invention. Thus, the design of a new polymer composition will be different depending on whether the Charpy test or the fatigue test according to the invention is chosen as the criterion. By way of example, composition C has a higher DBT than composition E. However, the latter has an NCF in fatigue (measured according to the process of the invention) that is lower than that of composition C. Thus, the fatigue test according to the invention makes it possible to demonstrate the advantage of composition C compared to composition E, for withstanding the actual fatigue conditions that exist in offshore flexible hoses.

The invention claimed is:

1. A process for evaluating the fatigue life of a polymer composition comprising the following steps:
   (i) providing a polymer composition;
   (ii) manufacturing several notched axisymmetric test specimens from said composition;
   (iii) subjecting said test specimens to a tensile fatigue test comprising several uniaxial loading and unloading cycles of the test specimen inducing triaxial stresses therein that simulate the stress conditions of the pressure sheath of a flexible pipe, in an off-shore application; and
   (iv) determining the number of cycles to failure for said polymer composition.

2. The process as claimed in claim 1, in which each test specimen is axisymmetric to the longitudinal axis z and has a maximum diameter d and a curved notch having a radius of curvature R, each test specimen having in its notched part a minimum radius a, the a/R ratio ranging from 0.05 to 10 and d being greater than 2a.

3. The process as claimed in claim 1, in which the tensile fatigue test consists of an elongation of the test specimen along the longitudinal axis, with a sinusoidal signal having a frequency ranging from 0.05 Hz to 5 Hz, at a temperature ranging from −15° C. to 23° C., the maximum elongation of one and the same tensile cycle being from 0.05 R to 1 R.

4. The process as claimed in claim 1, in which the minimum elongation of one and the same tensile cycle is greater than or equal to 0 up to 0.25 R.

5. The process as claimed in claim 1, in which: the radius of curvature R of the notch varies from 0.5 mm to 10 mm, the minimum radius a varies from 0.5 mm to 5 mm; and the maximum diameter d varies from 2 mm to 30 mm.

6. The process as claimed in claim 1, in which the maximum elongation along the longitudinal axis z varies from 0.2 mm to 4 mm.

7. The process as claimed in claim 1, in which the ratio between the minimum elongation and the maximum elongation of the cycle varies from 0 up to 0.8.

8. The process as claimed in claim 1, in which said number of cycles to failure is a number that represents the mean for a minimum of 2 test specimens.

9. The process as claimed in claim 1, in which the polymer composition comprises at least one semicrystalline thermoplastic polymer having a glass transition temperature ($T_g$) of less than or equal to 130° C.

10. The process as claimed in claim 1, in which the polymer composition comprises a fluoropolymer.

11. A process for manufacturing pipes or conduits intended to transport a pressurized and/or corrosive fluid, comprising:
   submitting polymer compositions to the process as claimed in claim 1,
   selecting a polymer composition having a mean number of cycles to failure of greater than 500,
   manufacturing said pipes or conduits from the polymer composition thus selected.

12. A flexible metal conduit comprising one or more metallic components and also at least one layer comprising the polymer composition selected by means of the process as claimed in claim 1, the number of cycles to failure of which is greater than 500, and one or more layers of a polymer material different from that of the polymer composition.

13. A method for simulating the triaxial stresses of a polymer material that goes into the composition of a pressure sheath for a flexible pipe intended for an offshore use, in which a notched axisymmetric test specimen is subjected to a tensile fatigue test comprising several loading and unloading cycles of the test specimen.

\* \* \* \* \*